United States Patent [19]

Friedlander et al.

[11] Patent Number: 5,071,862
[45] Date of Patent: Dec. 10, 1991

[54] 2-(3-OXYPYRIDINYL)-1,3-DIOXOLANE AND DIOXANE COMPOUNDS, COMPOSITIONS CONTAINING SAME AND PROCESS FOR CONTROLLING FUNGI USING SAME

[75] Inventors: Barry T. Friedlander, Guelph, Canada; Robert A. Davis, Cheshire, Conn.

[73] Assignees: Uniroyal Chemical Company, Inc., Middlebury, Conn.; Uniroyal Chemical Ltd./Ltee., Don Mills, Canada

[21] Appl. No.: 603,969

[22] Filed: Oct. 26, 1990

[51] Int. Cl.$^5$ ............... A61K 31/44; C07D 405/12
[52] U.S. Cl. ....................... 514/336; 546/268; 546/283
[58] Field of Search ............... 546/283, 268; 514/336

[56] References Cited

U.S. PATENT DOCUMENTS 4,859,687 8/1989 Riebli .................. 546/283

Primary Examiner—Jane T. Fan
Attorney, Agent, or Firm—Glenn E. Karta

[57] ABSTRACT

A compound having the structural formula

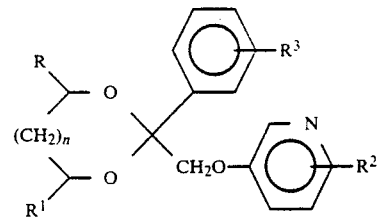

where R and $R^1$ are the same or different and are hydrogen or $C_1-C_6$ alkyl; $R^2$ is hydrogen, chlorine or bromine; $R^3$ is hydrogen, $C_1-C_6$ alkyl, $C_1-C_6$ alkoxy, halogen, trihalomethyl, nitro, cyano, phenyl, phenyl subsituted with $C_1-C_4$ alkyl, $C_1-C_4$ alkoxy, halogen, trihalomethyl, nitro or cyano, phenoxy or phenoxy subsituted with $C_1-C_4$ alkyl, $C_1-C_4$ alkoxy, halogen, trihalomethyl, nitro or cyano; and n is 0 or 1 is disclosed. A composition which comprises a fungicidally effective amount of the compound and a carrier therefor is also set forth. In addition, a process for controlling phytopathogenic fungi wherein a fungicidally effective amount of the compound is applied to the locus to be protected is described.

8 Claims, No Drawings

2-(3-OXYPYRIDINYL)-1,3-DIOXOLANE AND DIOXANE COMPOUNDS, COMPOSITIONS CONTAINING SAME AND PROCESS FOR CONTROLLING FUNGI USING SAME

BACKGROUND OF THE DISCLOSURE

1. Field of the Invention

The present invention is directed to a new class of substituted 2-(3-oxypyridinyl)-1,3-dioxolane and -1,3-dioxane compounds. More specifically, the present invention is directed to a new class of the above noted compounds having particular utility as fungicides.

The control of phytopathogenic fungi is of great economic importance not only because fungal growth on plants or on parts of plants such as fruit, blossoms, foliage, stems, tubers, roots and the like inhibit plant production, including the plant's commercially significant portions, such as foliage, fruit and seed, but, in addition, because fungi reduce the overall quality of the plant crop.

To control or at least reduce the detrimental effects of fungi, plants have long been treated with fungicides. However, the enormous economic toll taken by known fungi, as well as the continuing development of new fungus strains resistant to known fungicides, establishes a continuing need to develop new and more effective fungicides which possess curative, preventative and systemic action to protect all manner of plants. In addition, these newly developed fungicides must not only provide the above-discussed protection against the detrimental effects of fungi but, negatively, must not possess properties which have adverse effects on the plants to be protected. Furthermore, new fungicides must not have adverse effects on the commercial exploitation of the crop of the plant protected. Finally, the fungicide must be free of characteristics which adversely affect the surrounding environment including the soil and the surroundings into which the fungicide is introduced.

The above remarks establish the need in the art for new compounds, distinguished from the compounds utilized in the prior art, that provide more effective fungicidal activity, without adverse effects on the plants to be protected or the environment in which the plants are grown, against the scourge of phytopathogenic fungi.

2. Background of the Prior Art

The prior art includes teachings directed to the use of oxypyridinium compounds that are useful as fungicides. One such reference is U.S. Pat. No. 4,143,144, issued to Tobol et al., which discloses certain 2-alkoxy- and 2,6-dialkoxy-4-halomethylpyridine compounds which find utility as fungicides. It is emphasized, however, that although the compounds of the '144 patent are oxypyridinium compounds, they have no relation to any class of substituted 1,3-dioxolanes or substituted 1,3-dioxanes.

Similarly, U.S. Pat. No. 4,678,504 to Schulz et al. sets forth another class of oxypyridinium compounds useful as fungicides. The compounds of Schultz et al. are salts of 0-substituted 3-oxypyridinium compounds. More specifically, Schulz et al. describes benzyl bromide salts of 3-tetradecyloxypyridine, 2,4'-difluorobenzylhydroxypyridine and the like. This class of salts, like the compounds of the Tobol et al. patent, teach the use of oxypyridinium compounds as fungicidal agents. However, there is no disclosure, suggestion or even hint of utilizing 1,3-dioxolane and 1,3-dioxane compounds which include substituted and unsubstituted 2-(3-oxypyridinyl) substituents.

BRIEF SUMMARY OF THE INVENTION

A new class of compounds have now been developed which not only provides excellent protection against the ravages of phytopathogenic fungi but does so without adversely affecting the plants to be protected or significantly altering the environmental conditions of the soil and the surroundings into which these fungicides are introduced.

In accordance with the present invention a new class of compounds having the structural formula

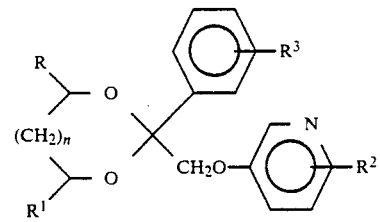

where R and $R^1$ are the same or different and are hydrogen or $C_1$–$C_6$ alkyl; $R^2$ is hydrogen, chlorine or bromine; $R^3$ is hydrogen, $C_1$–$C_6$ alkyl, $C_1$–$C_6$ alkoxy, halogen, trihalomethyl, nitro, cyano, phenyl, phenyl substituted with $C_1$–$C_4$ alkyl, $C_1$–$C_4$ alkoxy, halogen, trihalomethyl, nitro, cyano, phenoxy or phenoxy substituted with $C_1$–$C_4$ alkyl, $C_1$–$C_4$ alkoxy, halogen, trihalomethyl, nitro or cyano; and n is 0 or 1 is disclosed.

In addition, a composition comprising a fungicidally effective amount of the compound of this invention and a carrier therefor is set forth.

Finally, the present invention is also directed to a process for controlling phytopathogenic fungi which comprises applying a fungicidally effective amount of the compound of this invention to the locus to be protected.

DETAILED DESCRIPTION

The compounds of the present invention have the structural formula (I)

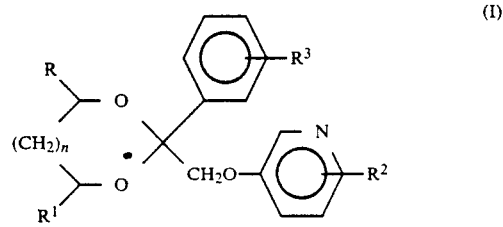

where R and $R^1$ are the same or different and are hydrogen or $C_1$–$C_6$ alkyl; $R^2$ is hydrogen, chlorine or bromine; $R^3$ is hydrogen, $C_1$–$C_6$ alkyl, $C_1$–$C_6$ alkoxy, halogen, trihalomethyl, nitro, cyano, phenyl, phenyl substituted with $C_1$–$C_4$ alkyl, $C_1$–$C_4$ alkoxy, halogen, trihalomethyl, nitro or cyano, phenoxy or phenoxy substituted with $C_1$–$C_4$ alkyl, $C_1$–$C_4$ alkoxy, halogen, trihalomethyl, nitro or cyano; and n is 0 or 1.

It is emphasized that the compound having the structural formula I encompasses dioxolanes, which correspond to the compound having the structural formula I where n is 0. The dioxolane compounds within the contemplation of the present invention have the structural formula

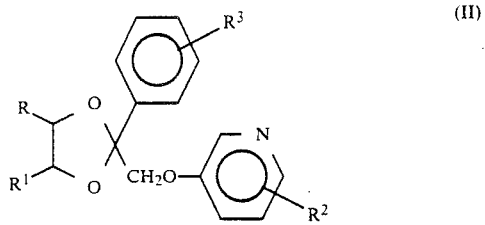

where R, R$^1$, R$^2$ and R$^3$ have the meanings given for the compound having the structural formula I.

The equally preferred dioxanes, within the contemplation of the present invention, are defined by the compound having the structural formula I where n is 1. The dioxanes of the present application have the structural formula

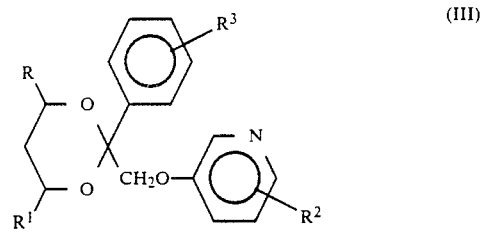

where R, R$^1$, R$^2$ and R$^3$ have the meanings given for the compound having the structural formula I.

The present invention also encompasses salts of the compound having the structural formula I. Salts within the contemplation of the subject invention are preferably addition products of the compound having the structural formula I, as well as compounds of structural formulae II and III within the genus of the compound having the structural formula I, and various acids. Among the preferred acids, which may be employed to produce salts of the present invention, are such inorganic acids as hydrochloric, hydrobromic, nitric and sulfuric acids. Organic acids, which also may be employed in the formation of salts within the contemplation of the present invention, include the sulfonic acids, methanesulfonic acid and p-toluenesulfonic acid. Of these acids, hydrochloric acid and methanesulfonic acid are particularly preferred in producing the salts of the subject invention.

A careful review of the structural formula I makes apparent to those skilled in the art that when R and R$^1$ are different, the carbon atom at the 2-position is asymmetrical. As such, this gives rise to optical isomers. Furthermore, in the case where either R or R$^1$ are not hydrogen, compounds having the structural formula I, or the subgeneric structural formulae II or III, may exist as geometric isomers in that R or R$^1$ are cis or trans relative to the substituents at the 2-position of the dioxolane or dioxane ring. It should therefore be appreciated that isomers, as well as mixtures of isomers, of the sort discussed above, are within the contemplation of the present invention.

Preferably, compounds having the structural formula I are characterized by R and R$^1$ being the same or different and being hydrogen or C$_1$-C$_4$ alkyl; R$^2$ being hydrogen or chlorine; R$^3$ being hydrogen, halogen, phenyl or phenoxy substituted with methyl, ethoxy, halogen or trifluoromethyl; and n is 0 or 1.

More preferably, the compound having the structural formula I is defined by R and R$^1$ being hydrogen or C$_1$-C$_3$ alkyl; R$^2$ being hydrogen, R$^3$ being chlorine, phenyl, or phenoxy substituted with halogen or trifluoromethyl; and n is 0 or 1. The latter definition, in the more preferred definition of the compound of the present invention, the definition of n being 0 or 1, emphasizes that no preference should be given over each other to the compounds having the structural formulae II and III.

The compound having the structural formula I is prepared in a two-step process wherein an alpha-haloketone having the structural formula

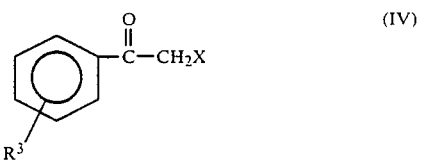

where X is halogen, preferably, bromine; and R$^3$ has the meanings given in the definition of structural formula I, is subjected to cyclization by reaction with a diol having the structural formula

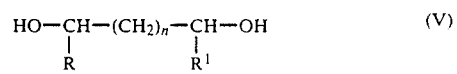

where R, R$^1$ and n have the meanings given in defining structural formula I.

The product of this cyclization reaction is a 2-halomethyl ketal having the structural formula

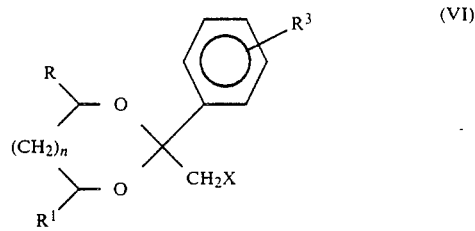

where R, R$^1$, R$^3$, X and n have the meanings given above. It is emphasized that details of this type of reaction are known in the art. For example, *Synthesis*, 1, 23, (1974) provides specifics of this reaction. The above referenced article is incorporated herein by reference.

The 2-halomethyl ketal compound having the structural formula VI is reacted with a 3-hydroxypyridine compound having the structural formula

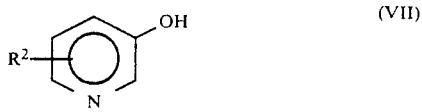

where R$^2$ has the same meanings as given for that substituent in structural formula I. This reaction occurs in the presence of an acid acceptor, preferably potassium carbonate. Moreover, the 3-hydroxypyridine compound having the structural formula VII is introduced into the reaction as a solution in which the solvent is preferably N,N-dimethylacetamide. The reaction usually occurs by refluxing the compounds having the structural formulae VI and VII at the boiling temperature of the solvent, usually N,N-dimethylacetamide, for a period of between about 6 hours and about 72 hours, preferably about 18 hours. The product of this reaction is the compound having the structural formula I.

Another aspect of the present invention is a composition which comprises a fungicidally effective amount of the compound having the structural formula I and a carrier therefor. Carriers within the contemplation of the composition of this invention may be liquids, solids or mixtures thereof.

Turning first to liquid carriers useful in producing the composition of the present invention, the liquid carrier may be a solvent or a dispersant. In addition, two liquid carriers can be utilized, one serving as a solvent and the other as a dispersant.

In the preferred embodiment wherein the composition is a solution, the solvent carrier is usually an organic compound which may be polar or non-polar. Solvents within the contemplation of the composition of this invention include acetone, methanol, isopropanol, t-butyl alcohol, cyclohexanone, n-butyl alcohol, toluene, xylene, dioxane, dimethylformamide, dimethylsulfoxide, ethylene dichloride and N-methylpyrrolidone.

Another class of liquid compositions within the contemplation of this invention is emulsions. An emulsion is formed when the compound having the structural formula I is dispersed in water in the presence of a surface active agent. An emulsion is preferably formed by first preparing a solution of the type discussed in the above paragraph. The solution is then dispersed in water and a surface active agent added thereto to form the emulsion. Surface active agents suitable for use in forming an emulsion within the contemplation of the composition of this invention are known to those skilled in the art. *McCutcheon's Detergents and Emulsifiers,* Allured Publishing Corp , Ridgewood, N.J. (1970); U.S. Pat. No. 2,514,916 and U.S. Pat. No. 2,547,734 provide examples of surface active agents useful in forming emulsions within the contemplation of the composition of this invention. The above recited references are incorporated herein by reference. As set forth in these references, the surface active agents may be anionic, cationic or non-ionic.

A third class of liquid compositions within the scope of this invention utilize a liquid dispersant as the carrier. In this embodiment, the compound having the structural formula I is dispersed in water in the absence of a surface active agent. Alternatively, the liquid composition involves a solution of the compound having the structural formula I, which, in turn, is dispersed in water, again in the absence of a surface action agent.

Yet another class of liquid compositions within the scope of the present invention utilizes an aerosol. An aerosol is liquid under pressure but is gaseous at atmospheric pressure and ambient temperature. In most instances an aerosol composition is prepared by first forming a solution of the compound having the structural formula I in a conventional solvent of the type discussed above. This solution is admixed with a volatile liquid aerosol under pressure in which condition the composition is applied.

A second major class of composition within the meaning of the present invention are solid compositions which employ a solid carrier. Solid carriers useful in the formation of the composition of this invention include dusts, granules, wettable powders, pastes and water soluble solids. For example, compositions within the contemplation of this invention may be applied as a dust when adsorbed or absorbed onto or mixed with a powdered, solid carrier. A solid carrier such as a mineral silicate, e.g., mica, talc, pyrophyllite and clays, may be utilized for this purpose.

Additional solid compositions can be prepared from granular formulations of the compound having the structural formula I and a granular or pelletized form of carrier such as granular clay, vermiculite, charcoal, corncobs or the like. The use of granular formulations is particularly suitable for application by broadcasting, side-dressing, soil incorporation or seed treatment.

A mixture of a solid and liquid composition, that employs both a liquid and a solid carrier, may also be used. Such a composition, for example, is prepared by dispersing a solid, on which the compound having the structural formula I is absorbed or adsorbed, in a liquid dispersant. Such a composition preferably includes a surface active agent to maintain the solid particles dispersed in the liquid dispersant.

It should be emphasized that the composition of the present invention may utilize a carrier which is itself active. That is, the carrier may be a plant growth regulant, an insecticide, an acaricide, a fungicide, a bacteriacide or the like.

The concentration of the compound having the structural formula I in the composition of this invention is a fungicidally effective amount. The exact concentration of a fungicidally effective amount depends upon such factors as the specific plant, or plants, which is to be protected, the fungus, or the fungi, which is to be controlled, soil conditions and chemistry and the climatic conditions under which the plant is grown. Generally, the concentration of Compound I, which is representative of a fungicidally effective amount, in the composition of the present invention may range from about 0.1% to about 95% by weight. However, when the compound having the structural formula I is applied as a spray, the dilution may be very high, resulting in a concentration as low as a few parts per million parts of composition. On the other hand, when ultra-low volume applications are employed, full strength concentrates may be utilized.

The present invention is also concerned with a process for controlling phytopathogenic fungi. In this process the compound having the structural formula I is applied to the locus under attack by said fungi in a fungicidally effective concentration.

In one preferred embodiment of the process of this invention the compound having the structural formula I is applied to the foliage of the plant or plants to be protected. This so-called "foliar treatment" is effectuated by applying the compound having the structural formula I to foliage at a concentration of between about 10 milligrams and about 500 milligrams of the compound per liter of inert liquid carrier.

In another preferred embodiment of the process of the present application, the process of controlling phytopathogenic fungi, a fungicidally effective amount of the compound having the structural formula I is applied to the soil in which the plant, or plants, to be protected from fungi is grown. In this method, the so-called "systemic treatment," the compound having the structural formula I is applied to the soil in a concentration of between about 0.125 and about 10 kilograms of compound per hectare of soil in which the plant, or plants, to be protected is grown. More preferably, systemic control involves application of between about 0.125 kg/ha and about 5 kg/ha of the compound having the structural formula I to the soil in which the plant, or plants, to be protected is grown.

Independent of which preferred process of controlling fungi is utilized, the application may be applied prior to or after infection by fungi. Furthermore, it should be appreciated that the exact dosage, applied systemically or directly to foliage, is dictated by the fungus to be controlled and the particular plant to be protected.

In another embodiment of the process of controlling phytopathogenic fungi utilizing the compound of the present invention, the compound having the structural formula I, the compound is applied as a coating to seeds of the plant to be protected. This embodiment of the process of the present invention provides the benefits of the two preferred embodiments discussed above, foliage treatment and systemic treatment. That is, the fungicidal coating, the coating of the compound having the structural formula I, protects the soil from infection by the fungi but is also taken up by the plants systemically to protect the plant from fungal attack. In this so-called "seed coating method," a concentration of the compound having the structural formula I in the range of between about 5 and about 75 grams per 100 kg. of seed is usually utilized.

The following examples are given to illustrate the scope of the present invention. Because these examples are given for illustrative purposes only, the scope of the instant invention should not be limited thereto.

EXAMPLE 1

Preparation of
3-[[2-([1,1'-Biphenyl]-4-yl)-1,3-dioxolan-2-yl]methoxy]-pyridine (Compound No. 2)

A mixture of 2-([1,1'-biphenyl]-4-yl)-2-(bromomethyl)-1,3-dioxolane (16 g.), 3-hydroxypyridine (5.7 g.) and potassium carbonate (9 g.) were refluxed with stirring in N,N-dimethylacetamide (75 ml.) for 18 hours. After refluxing, the mixture was allowed to cool and was thereafter poured into water (150 ml.). The resultant aqueous solution was extracted twice with ether. The combined ether fractions were washed once with 5% aqueous sodium hydroxide and 4 times with water. The washed ether fractions were then dried, filtered and the solvent evaporated to yield 3-[[2-([1,1'-biphenyl]-4-yl)-1,3-dioxolan-2-yl]methoxy]pyridine as an oil.

EXAMPLE 2

Preparation of 3-[2 ([1,1'-Biphenyl]-4-yl)-1,3-dioxolan-2-yl]-methoxy]pyridine hydrochloride (Compound No. 1)

The compound of Example 1, 3-[[2-([1,1'-biphenyl]-4-yl)-1,3-dioxolan-2-yl]methoxy]pyridine (3 g.) was formed into a solution by being dissolved in dry ether (250 ml.). The solution was cooled in an ice bath and dry hydrogen chloride gas was bubbled into the solution. This resulted in precipitation. When precipitation was ended, the solid was isolated by filtration and crushed to give a fine powder. The powder was identified as the titled compound having a melting point of 191° C. to 193° C.

EXAMPLE 3

Preparation of
3-[[2-(4-Bromophenyl)-1,3-dioxolan-2-yl-]-methoxy]-pyridine methanesulfonate (Compound No. 7)

A mixture of 2-(bromomethyl)-2-(4-bromophenyl)-1,3-dioxolane (25.5 g.), 3-hydroxypyridine (9.0 g.) and potassium carbonate (14.2 g.) in N,N-dimethylacetamide (125 ml.) was refluxed for 18 hours with stirring. Upon completion of this refluxing the mixture was allowed to cool. To this cooled reaction mixture was added water (250 ml.) and extracted with two portions of ether. The combined ether fractions were washed once with 5% aqueous sodium hydroxide and four times with water. The resulting ether layer was dried, filtered and evaporated resulting in the formation of an oil (18.5 g.).

A solution of this oil (3 g.) in dry ether was prepared and cooled in an ice bath. To this cooled solution was added methanesulfonic acid (0.9 g.) by dropwise addition accompanied by stirring. The resulting precipitate was obtained by filtration. After drying, the product, having a melting point of 133° C. to 134° C., was identified as 3-[[2-(4-bromophenyl)-1,3-dioxolan-2-yl]methoxy]pyridine methanesulfonate.

EXAMPLE 4

Preparation of
3-[[2-([1,1'-biphenyl]-4-yl)-4,5-dimethyl-1,3-dioxolan-2-yl]methoxy]pyridine (Compound No. 15)

A mixture of 2-([1,1'-biphenyl]-4-yl-2-(bromomethyl)-1,3-dioxolane (10 g.), 3-hydroxypyridine (4.7 g.) and potassium carbonate (5.2 g.) was refluxed with stirring for 18 hours. At the completion of this period, the mixture was cooled to ambient temperature. Water (250 ml.) was added to the cooled mixture and extracted with toluene. The resultant toluene solution was washed with water, then dried, filtered and evaporated to yield 3-[[2-([1,1'-biphenyl]-4-yl)-4,5-dimethyl-1,3-dioxolan-2-yl]methoxy]pyridine as an oil.

EXAMPLE 5

Preparation of
3-[[2-(2,4-Dichlorophenyl)-4-methyl-1,3-dioxolan-2-yl]methoxy]pyridine (Compound No. 18)

A mixture of 2-(bromophenyl)-2-(2,4-dichlorophenyl)-4-methyl-1,3-dioxolane (10 g.), 3-hydroxypyridine (3.8 g.) and potassium carbonate (5.5 g.) in N,N-dimethylacetamide (90 ml.) was refluxed with stirring for 18 hours. After the mixture was allowed to cool, it was poured into water and extracted with toluene. The toluene fraction, thereby obtained, was washed with 5% aqueous sodium hydroxide and evaporated to yield 3-[[2-(2,4-dichlorophenyl)-4-methyl-1,3-dioxolan-2-yl]methoxy]pyridine as an oil.

EXAMPLE 6

Preparation of
3-[[2-[4-[3-(Trifluoromethyl)phenoxy]phenyl]-1,3-dioxolan-2-yl]methoxy]pyridine hydrochloride (Compound No. 22)

A mixture of 2-(bromomethyl)-2-[4-[3-(trifluoromethyl)phenoxy]phenyl]-1,3-dioxolane (8 g.), 3-hydroxypyridine (2.4 g.) and potassium carbonate (3.5 g.) in N,N-dimethylacetamide (40 ml.) was refluxed for 18 hours with stirring. The reaction mixture was allowed to cool, poured into water and extracted twice with toluene. The combined toluene fractions were washed once with 5% aqueous sodium hydroxide and three times with water. The toluene fraction was then dried, filtered and evaporated to yield an oil (5.3 g.).

A portion of the thus obtained oil (2 g.) was dissolved in ether and dry hydrogen chloride gas was bubbled into the solution. This resulted in material oiling out of the solution. The material oiled out of the solution was cooled resulting in the solidification of the oil. This solid was isolated by filtration and identified as 3-[[2-[4-[3-(trifluoromethyl)phenoxy]phenyl]-1,3-dioxolan-2-yl]methoxy]pyridine hydrochloride. This product was obtained as a gray powder and was identified by its melting point of 138° C. to 140° C.

EXAMPLE 7

Preparation of Compounds Nos. 3–6, 8–14, 16, 17, 19–21 and 23–29

Compound Nos. 3–6, 8–14, 16, 17, 19–21 and 23–29 were prepared in accordance with the procedure used in Examples 1 to 6. They resulted in the formation of compounds whose identity is summarized in Table I. Table I identifies not only the compounds of this example but also the compounds synthesized in Examples 1 to 6. These compounds, Compound Nos. 1 to 29, are identified by their structural formula wherein the substituents are defined in Table I. Those compounds which are salts are further defined by the identity of the acid which is employed to form the salt. In addition, those compounds which are solid at ambient conditions are defined by their melting point. Table II identifies those compounds listed in Table I as being an oil at ambient conditions by their nuclear magnetic resonance spectroscopy data.

TABLE I

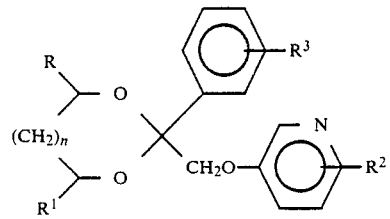

| Cpd. No. | n | R | $R^1$ | $R^2$ | $R^3$ | Salt | MP(°C.) |
|---|---|---|---|---|---|---|---|
| 1 | 0 | H | H | H | 4-Ph | HCl | 191–193 |
| 2 | 0 | H | H | H | 4-Ph | | Oil |
| 3 | 0 | H | H | H | 2,4-Cl$_2$ | | Oil |
| 4 | 0 | H | H | H | 4-Br | | Oil |
| 5 | 0 | H | H | H | 2-Cl | | Oil |
| 6 | 0 | H | H | H | 4-CH$_3$ | CH$_3$SO$_3$H | 104–106 |
| 7 | 0 | H | H | H | 4-Br | CH$_3$SO$_3$H | 133–134 |
| 8 | 0 | H | H | H | 4-C(CH$_3$)$_3$ | HCl | 134–137 |
| 9 | 0 | CH$_3$CH$_2$CH$_2$ | H | H | H | | Oil |
| 10 | 0 | CH$_3$CH$_2$ | H | H | H | | Oil |
| 11 | 0 | CH$_3$ | CH$_3$ | H | H | | Oil |
| 12 | 0 | CH$_3$ | H | H | 4-Ph | | Oil |
| 13 | 0 | CH$_3$ | H | H | 4-Cl | | Oil |
| 14 | 0 | CH$_3$ | H | H | 2-Cl | | Oil |
| 15 | 0 | CH$_3$ | CH$_3$ | H | 4-Ph | | Oil |
| 16 | 0 | H | H | H | 4-F | HCl | 168–172 |
| 17 | 0 | CH$_3$CH$_2$ | H | H | 4-Ph | | Oil |
| 18 | 0 | CH$_3$ | H | H | 2,4-Cl$_2$ | | Oil |
| 19 | 0 | CH$_3$CH$_2$ | H | H | 2,4-Cl$_2$ | | Oil |
| 20 | 0 | H | H | H | 4-(4-CH$_3$OPh) | | Oil |
| 21 | 0 | H | H | H | 4-(3-CF$_3$OPh) | | Oil |
| 22 | 0 | H | H | H | 4-(3-CF$_3$OPh) | HCl | 138–140 |
| 23 | 0 | CH$_3$ | H | H | 4-(3-CF$_3$OPh) | | Oil |
| 24 | 0 | CH$_3$ | H | H | 4-(2,4-Cl$_2$OPh) | | Oil |
| 25 | 0 | H | H | H | 4-(2-CH$_3$CH$_2$OOPh) | | Oil |
| 26 | 0 | H | H | 2-Br | 4-(4-FOPh) | HCl | 73–78 |
| 27 | 0 | H | H | 2-Cl | 4-(4-BrOPh) | | Oil |
| 28 | 0 | H | H | 2-Cl | 4-(4-ClOPh) | | Oil |
| 29 | 1 | H | H | 5-Cl | 2,4-Cl$_2$ | HCl | 128–129 |

Remarks:
Ph is phenyl
OPh is phenoxy

TABLE II

| Cpd No. | NMR data (δ) for CDCl$_3$ |
|---|---|
| 2 | 8.1–8.4(m, 2H), 7.0–7.7(m, 11H), 4.3(s, 2H), 3.7–4.3(m, 4H) |
| 3 | 8.1–8.4(m, 2H), 7.7(d, 1H), 7.0–7.5(m, 4H), 4.4(s, 2H), 3.7–4.3(m, 4H) |
| 4 | 8.1–8.3(m, 2H), 7.4(s, 4H), 7.1–7.3(m, 2H), 4.2(s, 2H), 3.8–4.2(m, 4H) |
| 5 | 8.4–8.4(m, 2H), 7.7–7.9(m, 1H), 7.1–7.4(m, 5H), 4.5(s, 2H), 3.8–4.3(m,4H) |
| 9 | 8.1–8.4(m, 2H), 7.1–7.7 (m, 7H), 4.2(s+s, 2H), 3.4–4.3(m, 3H), 0.8–1.8(m, 7H) |
| 10 | 8.1–8.4(m, 2H), 7.1–7.7(m, 7H), 4.2(s+s, 2H), 3.4–4.4 (m, 3H), 1.3–1.8(m, 2H), 0.8–1.2(m, 3H) |
| 11 | 8.1–8.4(m, 2H), 7.1–7.7(m, 7H), 4.2(s, 2H), 3.4–4.1(m, 2H), 2.3(d, 3H), 1.2(d, 3H) |
| 12 | 8.1–8.5(m, 2H), 7.1–7.7(m, 11H), 4.2(s+s, 2H), 3.5–4.2(m, 3H), 1.3(d+d, 3H) |
| 13 | 8.1–8.4(m, 2H), 7.1–7.7(m, 6H), 4.2(s+s, 2H), 3.5–4.6 (m, 3H), 1.3(d+d, 3H) |
| 14 | 8.1–8.4(m, 2H), 7.1–7.9(m, 6H), 4.5(s+s, 2H), 3.4–4.5(m, 3H), 1.3(d+d, 3H) |
| 15 | 8.1–8.4(m, 2H), 7.2–7.7(m, 11H), 4.2(s, 2H), |

TABLE II-continued

| Cpd No. | NMR data (δ) for CDCl₃ |
|---|---|
|  | 3.5–4.1(m, 2H), 1.4(d, 3H), 1.2(d, 3H) |
| 17 | 8.0–8.6(m, 2H), 7.1–7.7(m, 11H), 4.2(s+s, 2H), 3.5–4.3(m, 3H), 1.3–2.0(m, 2H), 0.8–1.2(m, 3H) |
| 18 | 8.1–8.3(m, 2H), 7.5–7.8(m, 1H), 7.1–7.4(m, 4H), 4.4(s+s, 2H), 3.3–4.4(m, 3H), 1.3(d+d, 3H) |
| 19 | 8.1–8.3(m, 2H), 7.5–7.8(m, 1H), 7.1–7.5(m, 4H), 4.4(s+s, 2H), 3.4–4.3(m, 3H), 1.3–1.9(m, 2H), 0.8–1.2(m, 3H) |
| 20 | 6.8–7.7(m, 12H), 4.3(s, 2H), 3.7–4.3(m, 4H), 2.3(s, 3H) |
| 21 | 8.0–8.7(m, 2H), 6.9–7.8(m, 10H), 4.3(s, 2H), 3.8–4.4(m, 4H) |
| 23 | 8.1–8.4(m, 2H), 6.9–7.7(m, 10H), 4.2(s+s, 2H), 3.5–4.6(m, 3H), 1.3(d+d, 3H) |
| 24 | 8.0–8.6(m, 2H), 6.8–7.7(m, 9H), 3.5–4.5(m, 6H), 1.3(d+d, 3H) |
| 25 | 8.1–8.4(m, 2H), 6.8–7.6(m, 10H), 4.2(s, 2H), 3.9(q, 2H), 3.8–4.2(m, 4H), 1.2(t, 3H) |
| 27 | 7.9–8.1(m, 1H), 6.8–7.7(m, 9H), 4.2(s, 2H), 3.9–4.3(m, 4H) |
| 28 | 7.8–8.0(m, 1H), 6.8–7.7(m, 9H), 4.2(s, 2H), 3.8–4.4(m, 4H) |

EXAMPLE 8

Preparation of Fungicidal Compositions

Each of Compound Nos. 1 to 24 (0.3 g.), summarized in Table I, were dissolved in acetone (10 ml.). Water and one or two drops of the emulsifying agent, Triton [trademark]X-100 were added to the thus formed solution to form an emulsion. The amount of water added was a function of the desired concentration of the emulsion composition which are hereinafter reported as milligrams per liter (mg/l).

EXAMPLE 9

Control of Powdery Mildew Fungus by Systemic Root Uptake

Compositions of Compound Nos. 1 to 29, formed in accordance with the procedure of Example 8, were tested to evaluate their effectiveness in preventing or controlling powdery mildew disease of barley caused by the fungus, *Erysiphe graminis* and powdery mildew disease of cucumber caused by the fungus, *Erysiphe cichoracearum*. This prevention root or control capability, utilizing the compounds of the present invention, was tested using the systemic uptake method of applying the fungicidal compositions to the plants to be protected.

In accordance with the aim of this test, pots (4×4×3.5 inches) containing ten plants of barley (Variety "Herta") or ten plants of cucumber (Variety "Marketmore 70") were grown to an age of six days and ten days, respectively. Upon reaching these ages, emulsion compositions (45 ml.) of Compound Nos. 1 to 29, formed in accordance with the procedure of Example 8, were added to each pot. That is, emulsion compositions (45 ml.) of each of the compounds of Table I was separately added to pots containing ten barley or ten cucumber plants of the type enumerated above. The emulsion compositions saturated the soil in each pot without significant loss through drainage into saucers below the pots. Each of the compositions contained one of Compound Nos. 1 to 29 in a concentration of 250 mg/l. A number of pots containing the barley and cucumber plants which were treated with the compounds of this invention were left untreated as controls.

The barley and cucumber plants in all the pots including those treated and those untreated, were inoculated with powdery mildew fungus 24 hours after treatment with the emulsion compositions containing Compound Nos. 1 to 29. Fungus inoculation was accomplished by tapping leaves of previously infected barley and cucumber plants over the treated and untreated pots containing the barley and cucumber plants, respectively, to distribute the spores of the fungus over the plants growing in the pots.

Six days after inoculation, disease control was evaluated on a 0 to 6 rating scale. A 0 rating was assigned when no disease was evidenced on the plant. A 6 rating was given for severe disease. Intermediate ratings were assigned depending on the degree of disease. Percent control was computed by comparing the ratings of the treated and untreated plants.

The results of this test are reported in Table III wherein systemic control of powdery, mildew disease in barley is reported under the title "BMS 250." Control of powdery mildew disease in cucumber is reported under the title "CMS 250."

EXAMPLE 10

Control of Powdery Mildew Fungus by Foliar Application

A large number of planting pots, identical with those utilized in Example 9, sufficient to accommodate testing in duplicate or triplicate for each of the 29 compounds tabulated in Table I, were each planted with eight barley plants (Variety "Larker"). There were enough planted pots so that for each treated pot there was at least one pot untreated which acted as a control.

Each of the treated pots were sprayed with emulsions of each of Compound Nos. 1 to 29 in a concentration of 1000 milligrams of the compound per liter of water (1000 mg/l). After the foliage of the sprayed barley plants were dried, all the plants, including the unsprayed control plants, were placed in a greenhouse maintained at 21° C. All the plants, controls as well as sprayed plants, were thereupon inoculated with powdery mildew fungus, *Erysiphe graminis*. Inoculation of the fungus was accomplished in accordance with the method utilized in Example 9.

Five days after inoculation, the plants were evaluated and assigned a disease rating of 0 to 6 in accordance with the criteria explained in Example 9. Percentage control was computed in accordance with the method utilized in Example 9. The results of this test are summarized in Table III under the title "BMP 1000."

EXAMPLE 11

Bean Rust Fungus Eradicant and Bean Powdery Mildew Protectant Test

Two pinto bean plants, *P. vulgaris*, were planted in a plurality of pots. When the plants were seven days old, at the primary leaf stage of growth, they were all sprayed with a suspension containing 20,000 spores of the bean rust fungus, *Uromyces phaseoli*, per milliliter of suspending water. All the pots containing the inoculated plants were than incubated in a controlled environmental chamber, maintained at 99% humidity and 21° C., for 24 hours to allow infection to develop. The plants were then moved from the incubator and allowed to dry.

Two days after inoculation the infected plants were separately sprayed with each of the emulsion compositions containing Compound Nos. 1 to 29, tabulated in Table I, prepared in accordance with the procedure of Example 8. Each of the emulsion compositions provided a dosage of 1,000 mg/l of the active compound. An equal number of infected plants, not sprayed, acted as controls. All the sprayed and unsprayed plants were placed in a greenhouse, maintained at a temperature of 21° C. for five days to allow any disease to be expressed. The treated plants were additionally tested for bean powdery mildew protectant use by inoculating all plants by tapping spores of Erysiphe polygoni mildew over the leaves.

The sprayed and unsprayed control plants were examined for disease which was assessed using the 0 to 6 rating system described in Example 9. Disease control, as explained in Example 9, was then determined. The control of disease, expressed as percent reduction of disease, is included in Table III under the titles "BRE 1000 and PMP 1000."

EXAMPLE 12

Control of Barley Blast by Foliar Treatment

A plurality of planting pots which included ten plants of six day old barley (Variety "Herta") were prepared. These pots were sprayed with the emulsion compositions, prepared in accordance with the procedure of Example 8, of each of Compound Nos. 1 to 29, set forth in Table I.

The plants in these pots, as well as an equal number of six day old Variety "Herta" barley plants in control pots, were inoculated with spores of the blast fungus, *Pyricularia oryzae*. The method of inoculation was identical with that utilized in Example 9.

All the fungus inoculated plants were placed in a greenhouse, maintained at a temperature of 21° C. and a humidity of 99%, for five days. At that time, the plants were evaluated on the 0 to 6 disease rating system, explained in Example 9. Percent control was computed by comparing the ratings of the sprayed and unsprayed plants. The results of this test are included in Table III under the title "BBL 1000."

EXAMPLE 13

Control of Nine Fungus Species

Each of the compounds included in Table I, Compound Nos. 1 to 29, were solubilized in acetone at a concentration of 500 mg/l. Filter paper discs, each 11 mm. in diameter, were immersed in each of the thus formed solutions. The discs were allowed to dry in air, thus driving off the acetone solvent. An equal number of discs were not immersed in these solutions and acted as controls.

Each of the treated and untreated disks were then placed in agar plates and the fungus species *Alternaria solani*, was added to the center of each paper disc in the form of a culture plug with the fungus mat in contact with the treated paper of the test disc or, in the case of the controls, in contact with the untreated filter test disc. The agar plates were incubated at 29° C. in an oven.

Upon removal from the oven, percent growth inhibition by the compounds of the fungus species was evaluated by measuring the radius from the center of the fungus colony of the treated discs compared to the radius from the center of the fungus colony of the untreated disks. That is, inhibition effectuated by each of the compounds was determined as a function of the percent difference between the radii of the treated and untreated discs. The results of these tests appear in Table III under the title "ALT 500."

In a similar fashion, the fungus species: *Botrytis cinerea, Fusarium oxysporum, Helminthosporium maydis, Phytophthora infestans, Sclerotinia sclerotiorum* and *Sclerotium rolfsii* were treated in exact accordance with the procedure utilized to test the fungus species, *Alternaria solani*. The effectiveness of Compound Nos. 1 to 29, in controlling these six fungus species are summarized in Table III under the titles "BOT 400," "FUS 500," "HMAY 500," "PHY 500," "SCM 500" and "SCO 500." These designations refer to the six fungus species in the order of their earlier recitation in the discussion of this example.

A separate test was utilized to determine the control of a ninth fungus species, *Cercospora arachidicola*. This species was tested by depositing two drops of a spore suspension of the fungus (20,000 spores per millimeter) to the above-discussed chemically treated discs rather then as a mycelial cell culture plug. Scoring of the effectiveness of the compounds in controlling the *Cercospora arachidicola* fungus was accomplished without the use of a control. A rating of 100 represented complete inhibition of germination and growth of the fungus; a rating of 80 represented nearly complete inhibition but some growth of the fungus; a rating of 50 represented partial inhibition but some growth or early complete inhibition with later growth; a rating 20 indicated some, but not significant, inhibition of growth; and a 0 rating indicated complete growth of the fungus without any inhibition. The rating of this species is included in Table III under the title "CER 500."

TABLE III

| | Percent Fungicidal Control | | | | | | | | | | | | | |
|---|---|---|---|---|---|---|---|---|---|---|---|---|---|---|
| Cpd. No. | ALT 500 | BBL 1000 | BMP 1000 | BMS 250 | BOT 500 | BRE 1000 | CER 500 | CMS 250 | FUS 500 | HMAY 500 | PHY 500 | PMP 1000 | SCH 500 | SCO 500 |
| 1 | 25 | 90 | 90 | 0 | 0 | 0 | 0 | 0 | 0 | 0 | 45 | 0 | 0 | 10 |
| 2 | 0 | 90 | 90 | 0 | 0 | 0 | 0 | 15 | 15 | 40 | 76 | 0 | 0 | 40 |
| 3 | 0 | 50 | 100 | 0 | 0 | 0 | 0 | 15 | 15 | 15 | 75 | 0 | 15 | 0 |
| 4 | 0 | 0 | 20 | 0 | 35 | 0 | 0 | 50 | 50 | 0 | 50 | 95 | 0 | 0 |
| 5 | 0 | 0 | 0 | 40 | 35 | 0 | 0 | 0 | 20 | 10 | 50 | 95 | 0 | 35 |
| 6 | 0 | 0 | 90 | 0 | 35 | 0 | 0 | 0 | 0 | 15 | 0 | 0 | 0 | 0 |
| 7 | 0 | 20 | 90 | 0 | 0 | 0 | 0 | 0 | 0 | 0 | 20 | 0 | 30 | 0 |
| 8 | 0 | 0 | 90 | 0 | 15 | 0 | 0 | 0 | 0 | 0 | 0 | 0 | 50 | 0 |
| 9 | 10 | 90 | 90 | 35 | 50 | 0 | 0 | 0 | 0 | 35 | 0 | 0 | 0 | 25 |
| 10 | 35 | 80 | 90 | 15 | 25 | 0 | 0 | 0 | 0 | 0 | 0 | 0 | 0 | 35 |
| 11 | 10 | 80 | 90 | 35 | 0 | 0 | 0 | 50 | 10 | 35 | 0 | 0 | 0 | 0 |
| 12 | 25 | 80 | 100 | 35 | 0 | 0 | 0 | 0 | 0 | 45 | 15 | 95 | 55 | 0 |
| 13 | 15 | 40 | 100 | 35 | 0 | 0 | 0 | 50 | 40 | 15 | 20 | 50 | 0 | 0 |
| 14 | 50 | 80 | 90 | 35 | 0 | 0 | 0 | 0 | 10 | 25 | 35 | 90 | 0 | 35 |
| 15 | 55 | 90 | 90 | 15 | 50 | 0 | 0 | 0 | 30 | 35 | 0 | 90 | 0 | 35 |
| 16 | 0 | 80 | 100 | 97 | 0 | 20 | 0 | 45 | 0 | 25 | 35 | 0 | 0 | 0 |

TABLE III-continued

| Cpd. No. | ALT 500 | BBL 1000 | BMP 1000 | BMS 250 | BOT 500 | BRE 1000 | CER 500 | CMS 250 | FUS 500 | HMAY 500 | PHY 500 | PMP 1000 | SCH 500 | SCO 500 |
|---|---|---|---|---|---|---|---|---|---|---|---|---|---|---|
| 17 | 35 | 50 | 90 | 0 | 0 | 0 | 0 | 0 | 0 | 60 | 35 | 0 | 0 | 0 |
| 18 | 40 | 0 | 90 | 0 | 0 | 75 | 0 | 0 | 0 | 0 | 60 | 80 | 0 | 30 |
| 19 | 25 | 15 | 90 | 0 | 0 | 25 | 0 | 0 | 0 | 0 | 0 | 90 | 0 | 0 |
| 20 | 10 | 15 | 85 | 60 | 55 | 0 | 0 | 0 | 0 | 10 | 15 | 0 | 60 | 35 |
| 21 | 0 | 65 | 90 | 0 | 70 | 0 | 0 | 0 | 0 | 0 | 0 | 0 | 0 | 0 |
| 22 | 0 | 50 | 90 | 0 | 100 | 0 | 0 | 0 | 0 | 20 | 50 | 0 | 0 | 25 |
| 23 | 0 | 15 | 90 | 0 | 0 | 0 | 0 | 0 | 0 | 10 | 0 | 0 | 0 | 0 |
| 24 | 0 | 85 | 85 | 0 | 0 | 0 | 0 | 0 | 0 | 35 | 0 | 0 | 0 | 0 |
| 25 | 40 | 90 | 100 | 0 | 0 | 0 | 0 | 0 | 0 | 0 | 0 | 70 | 0 | 0 |
| 26 | 40 | 100 | 0 | 15 | 0 | 0 | 0 | 0 | 0 | 0 | 0 | 0 | 0 | 0 |
| 27 | 20 | 85 | 75 | 10 | 0 | 0 | 0 | 0 | 0 | 0 | 0 | 0 | 0 | 0 |
| 28 | 30 | 90 | 35 | 0 | 10 | 0 | 0 | 0 | 10 | 25 | 15 | 0 | 10 | 0 |
| 29 | 0 | 0 | 100 | 15 | 30 | 0 | 0 | 50 | 5 | 45 | 5 | 0 | 5 | 55 |

The above embodiments and examples are given to illustrate the scope and spirit of the instant invention. These embodiments and examples will make apparent, to those skilled in the art, other embodiments and examples. These other embodiments and examples are within the contemplation of the present invention. Therefore, this invention should be limited only by the appended claims.

What is claimed is:

1. A compound having the structural formula

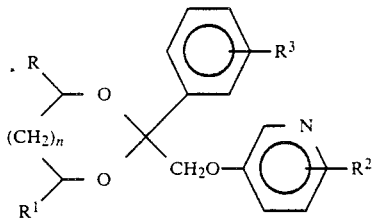

where R and $R^1$ are the same or different and are hydrogen or $C_1$-$C_6$ alkyl; $R^2$ is hydrogen, chlorine or bromine; $R^3$ is hydrogen, $C_1$-$C_6$ alkyl, $C_1$-$C_6$ alkoxy, halogen, trihalomethyl, nitro, cyano, phenyl, phenyl substituted with $C_1$-$C_4$ alkyl, $C_1$-$C_4$ alkoxy, halogen, trihalomethyl, nitro or cyano, phenoxy or phenoxy substituted with $C_1$-$C_4$ alkyl, $C_1$-$C_4$ alkoxy, halogen, trihalomethyl, nitro or cyano; and n is 0 or 1.

2. A compound in accordance with claim 1 wherein R and $R^1$ are the same or different and are hydrogen or $C_1$-$C_4$ alkyl; $R^2$ is hydrogen or chlorine; $R^3$ is hydrogen, halogen, phenyl or phenyl substituted with methyl, ethoxy, halogen or trifluoromethyl.

3. A compound in accordance with claim 2 where R and $R^1$ are the same or different and are hydrogen or $C_1$-$C_3$ alkyl; $R^2$ is hydrogen; $R^3$ is chlorine, phenyl or phenoxy substituted with halogen or trifluoromethyl.

4. An organic or inorganic acid addition salt of the compound of claim 1.

5. A salt in accordance with claim 4 wherein said acid is hydrochloric acid or methanesulfonic acid.

6. A composition comprising a fungicidally effective amount of the compound of claim 1 and a carrier therefor.

7. A composition comprising a fungicidally effective amount of the salt of claim 4 and a carrier therefor.

8. A method for controlling phytopathogenic fungi comprising applying a fungicidally effective amount of the compound of claim 1 to the locus under attack by phytopathogenic fungi.

* * * * *